United States Patent [19]

Friddell

[11] Patent Number: 5,033,073
[45] Date of Patent: Jul. 16, 1991

[54] SYSTEM FOR RADIOGRAHICALLY INSPECTING A RELATIVELY STATIONARY OBJECT AND RELATED METHOD

[75] Inventor: Kenneth D. Friddell, Seattle, Wash.

[73] Assignee: Boeing Company, Seattle, Wash.

[21] Appl. No.: 261,135

[22] Filed: Oct. 24, 1988

Related U.S. Application Data

[63] Continuation-in-part of Ser. No. 124,616, Nov. 24, 1987, Pat. No. 4,974,247.

[51] Int. Cl.$^5$ .............................................. G21K 5/10
[52] U.S. Cl. ..................................... 378/146; 378/45; 378/62; 378/88
[58] Field of Search ............................ 378/45, 62–63, 378/86–88, 145, 146, 156, 160

[56] References Cited

U.S. PATENT DOCUMENTS

| | | | |
|---|---|---|---|
| Re. 28,544 | 9/1975 | Stein et al. | 378/57 |
| Re. 32,164 | 5/1987 | Kruger | 378/22 |
| 1,961,713 | 6/1934 | Simjian | 378/146 |
| 2,730,566 | 1/1956 | Bartow et al. | 378/87 |
| 3,854,049 | 12/1974 | Mistretta et al. | 378/62 |
| 4,179,100 | 12/1979 | Sashin et al. | 378/146 |
| 4,342,914 | 8/1982 | Bjorkholm | 378/99 |
| 4,352,986 | 10/1982 | Pfeiler | 378/146 |
| 4,761,802 | 8/1988 | Kiri | 378/146 |
| 4,773,087 | 9/1988 | Plewes | 378/146 |
| 4,839,913 | 6/1989 | Annis et al. | 378/87 |

Primary Examiner—Carolyn E. Fields
Assistant Examiner—David P. Porta
Attorney, Agent, or Firm—Finnegan, Henderson, Farabow, Garrett and Dunner

[57] ABSTRACT

An improved system for radiographically inspecting a relatively stationary object and a related method are disclosed. A source transmits radiation toward a selected location at which the object is positioned. Radiation interactive with the object is thereafter transmitted in one embodiment to a detection area having electronic detectors and another embodiment through an atomic element filter to the detection area. En route to the detectors area or the filter and detection area, radiation is first blocked by a scanning point selection means which sequentially selects only a pencil beam portion of the radiation to be transmitted to the detection area at any given time. The pencil beams sequentially selected sweep the entire detection area over a short time, enabling use of signals generated by the electronic detectors in obtaining an image of the object or for obtaining the identity and location of atomic elements constituting the object.

35 Claims, 8 Drawing Sheets

FIG. 2
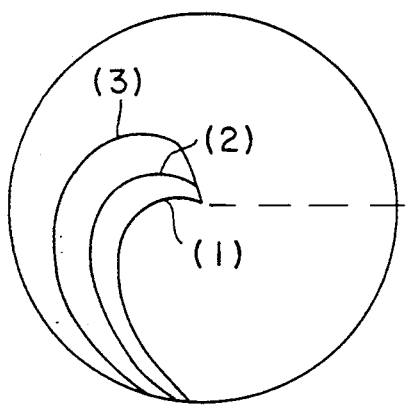
22
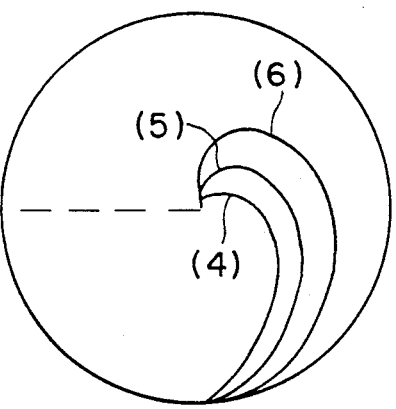
24
(1) $R_1 = a \times \sqrt{\theta}$
(2) $R_1 = a \times \theta$
(3) $R_1 = a \times \theta^2$
(4) $R_2 = a \times \sqrt{\pi - \theta}$
(5) $R_2 = a \times (\pi - \theta)$
(6) $R_2 = a \times (\pi - \theta)^2$ □ 50 KEV .001 cm CU    + 100 KEV .04 cm Cu > # SYSTEM FOR RADIOGRAHICALLY INSPECTING A RELATIVELY STATIONARY OBJECT AND RELATED METHOD This application is a continuation-in-part of U.S. patent application Ser. No. 124,616 filed Nov. 24, 1987 now U.S. Pat. No. 4,974,247.

I. FIELD OF THE INVENTION

This invention relates generally to a system and related method for inspecting an object, and more specifically, a system and related method for radiographically inspecting a relatively stationary object positioned at a selected location to generate a radiographic image of the object.

II. BACKGROUND INFORMATION

Known systems for performing radiographic inspection of an object include systems which utilize X-ray film. Such inspection systems generally produce high resolution images of the object being inspected, but present a disadvantage in that such systems perform radiographic reproduction over a limited dynamic range. The high resolution of the X-ray film results from the fact that individual silver bromide crystals, which make up the emulsion layer of the X-ray film and which are activated by incident X-rays to create a "picture," are of relatively small size. The dynamic range, on the other hand, is determined by the number of silver bromide crystals per unit area in the emulsion layer that can be exposed to the X-ray radiation. The dynamic range of a given film is limited by the thickness of the silver bromide crystal emulsion that, when developed, will not allow detectable light to be transmitted. The use of higher density film having high dynamic range necessitates the use of a very intense light source for reading the X-ray piCture. This requirement for a very intense light for reading the X-ray film presents a significant disadvantage as to the use of such film. Also, the use of X-ray film for radiographic inspection does not permit compensation for the effects of radiation scattered by the object being inspected.

To increase the dynamic range for radiographic inspection systems and to permit compensation for radiation scatter, radiation detectors that produce a linear electronic signal response, when exposed to a wide range of X-ray intensities, in conjunction with electronic processing of the signals with wide range linear amplifiers are used.

An example of a known radiographic inspection system, which utilizes electronic detectors, is a "linear flying spot scanner" of the type commonly used for inspecting luggage at airports. This linear flying spot scanner includes a radiation source, a stationary shield, a rotating beam-chopper wheel and electronic detectors. The radiation source transmits a beam of radiation along a path toward a selected location at which an object is positioned. The stationary shield, rotating beam-chopper wheel and the electronic detectors are disposed in the radiation path, with the stationary slit and beam-chopper wheel positioned between the radiation source and the electronic detectors.

The stationary shield and beam-chopper wheel are aligned to select a portion of the radiation beam from the source. This portion of the radiation beam is transmitted along the radiation path to a single portion of the selected location at which the object is positioned and to a corresponding selected portion or area of the object.

Radiation transmitted to the selected area of the object interacts with the selected area. A portion of the radiation interactive with the area of the object is compton scattered in all directions. Another portion is absorbed by the photoelectric interaction in the object and re-emitted in all directions as fluorescent radiation, while yet another portion passes through the object. X-ray sensitive electronic detectors, disposed between the radiation source and the object, generate signals in response to the fluorescent and compton scattered radiation which is scattered in the backward direction by the selected area of the object, and through-radiation detectors, positioned such that the object is between the radiation source and the through-radiation detectors, generate response signals for radiation passing through the selected area of the object.

Response signals generated by the electronic detectors are processed to obtain a data representation of the selected area of the object. The signal processing is performed by a data processor. An image of the object area is obtained using the processed signal data, and using a visual display means which is responsive to the processed data, the image of the selected area of the object is displayed.

As described above, the stationary shield and beam chopper wheel select a single line portion of the selected location and thereby allow radiation to be transmitted to just a corresponding selected area of the object. By limiting the portion of the object to which radiation is transmitted, the exposure of the object to radiation is limited. The number of detectors required to generate response signals is also minimized by limiting the radiation transmitted to the object and, thus, just a few large area detectors are utilized. The resolution of such a system is determined by the size of the slits in the stationary shield and the rotating chopper wheel.

However, because the linear flying spot scanner only operates to select a single line portion of the selected location and a single corresponding object area, the necessity exists to move the object through the selected inspection location in order to radiographically inspect area of the object other than the single line selected area. Such movement places successive line areas of the object in the selected location to which radiation is transmitted and thereby permits a radiographic image of each line area of the object to be obtained.

The requirement of moving the object relative to the linear flying spot scanner is a major disadvantage in that, in order to move the object, specialized moving apparatus is needed. Furthermore, space must be provided with the linear flying spot scanner to accommodate the moving apparatus.

Alternatively, certain known radiographic inspection systems utilize a collimated linear array of electronic detectors. The electronic detectors are moved relative to the object and radiation source to successively generate response signals for the successive sections or areas of the object. The radiation source of such a system transmits radiation toward the entire object being inspected, permitting the detector array, as moved, to generate response signals for each section of the object. The moving detector system requires a large number of electronic detectors to inspect the object to ensure high resolution. The major disadvantages of such a system are the need to move the detectors relative to the object and the large number of detectors and associated electronics. The detectors must be balanced for uniform response characteristics.

SUMMARY OF THE INVENTION

The present invention has as an object to provide a radiographic inspection system which does not have the limited dynamic range of X-ray film inspection systems and which may be used to minimize the effects of fluorescent and compton scattered radiation.

The present invention also has as an object providing a radiographic inspection system which does not require movement of either the object or the electronic detectors relative to the rest of the inspection system in order to obtain a radiographic representation of the entire object.

The present invention has a further object the provision of such a radiographic inspection system having the capability of determining the atomic elements and atomic element distribution within the object.

Additional objects and advantages of the invention will be set forth in the description which follows, and in part will be obvious from the description or may be learned by practice of the invention. The objects and advantages of the invention may be realized and obtained by means of the intrumentalities and combinations particularly pointed out in the appended claims.

To achieve the foregoing objects, and in accordance with the purposes of the invention as embodied and broadly described herein, there is provided a system for radiographically inspecting a predetermined area of a relatively stationary object positioned at a selected location, comprising: a source of radiation operative to transmit along a radiation path toward the selected location a first radiation beam having a cross-sectional area at least corresponding to the predetermined inspection area; detection means, having a detection area at least corresponding to the predetermined inspection area, disposed in the radiation path in alignment with the first radiation beam; scanning point selection means, disposed in the radiation path between the radiation source and detection means, for sequentially selecting and transmitting selected portions of the cross-sectional area of the first radiation beam for striking in sequence corresponding portions of the detection area of the detection means, each selected portion of the cross-sectional area of the first radiation beam corresponding to a pencil beam of radiation, the detection means being responsive to each selected portion of the first radiation beam striking a corresponding portion of the detecting area for generating signals corresponding to radiation interactive with a corresponding portion of the predetermined inspection area of an object at the selected location; position encoder means responsive to said scanning point selection means for determining the position of each selected portion of the first radiation beam; data processing means responsive to said position encoder means and said detecting means for processing the signals generated by the detection means; and display means governed by said data processing means for generating a radiographic image of the predetermined area of the object.

In another aspect, such a system further comprises means for filtering the first radiation beam disposed in the radiation path between the radiation source and the scanning point selection means for causing the display means to generate a representation of the various atomic element groups in the predetermined area of the object.

A related method is also provided. The method, for radiographically inspecting a predetermined area of a stationary object positioned at a selected location, comprises the steps of: transmitting a first radiation beam having a cross-sectional area at least corresponding to the predetermined inspection area along a radiation path in a direction toward the selected location; selecting, sequentially, portions from the cross-sectional area of the first radiation beam and transmitting the selected portions along the radiation path to the selected location, each said selected portion of the cross-sectional area of the first radiation beam comprising a pencil beam of radiation; detecting each of the selected portions of the first radiation beam striking corresponding portions of the predetermined inspection area of an object at the selected locations and generating signals in response to the radiation striking the corresponding portions; determining the position of each selected portion of the first radiation beam; processing the signals generated in response to the radiation striking the corresponding portions; and generating a radiographic image of the predetermined area of the object.

In another aspect the related method further comprises the step of filtering each selected portion of the cross-sectional area to determine a corresponding atomic element group.

BRIEF DESCRIPTION OF THE DRAWINGS

FIG. 2 is a schematic diagram of a pair of rotating disks, showing spiral slits therein, which are used in the radiographic inspection system of the present invention;

DESCRIPTION OF THE PREFERRED EMBODIMENTS

Reference will now be made in detail to present preferred embodiments of the invention, examples of which are illustrated in the accompanying drawings.

Figure 1:
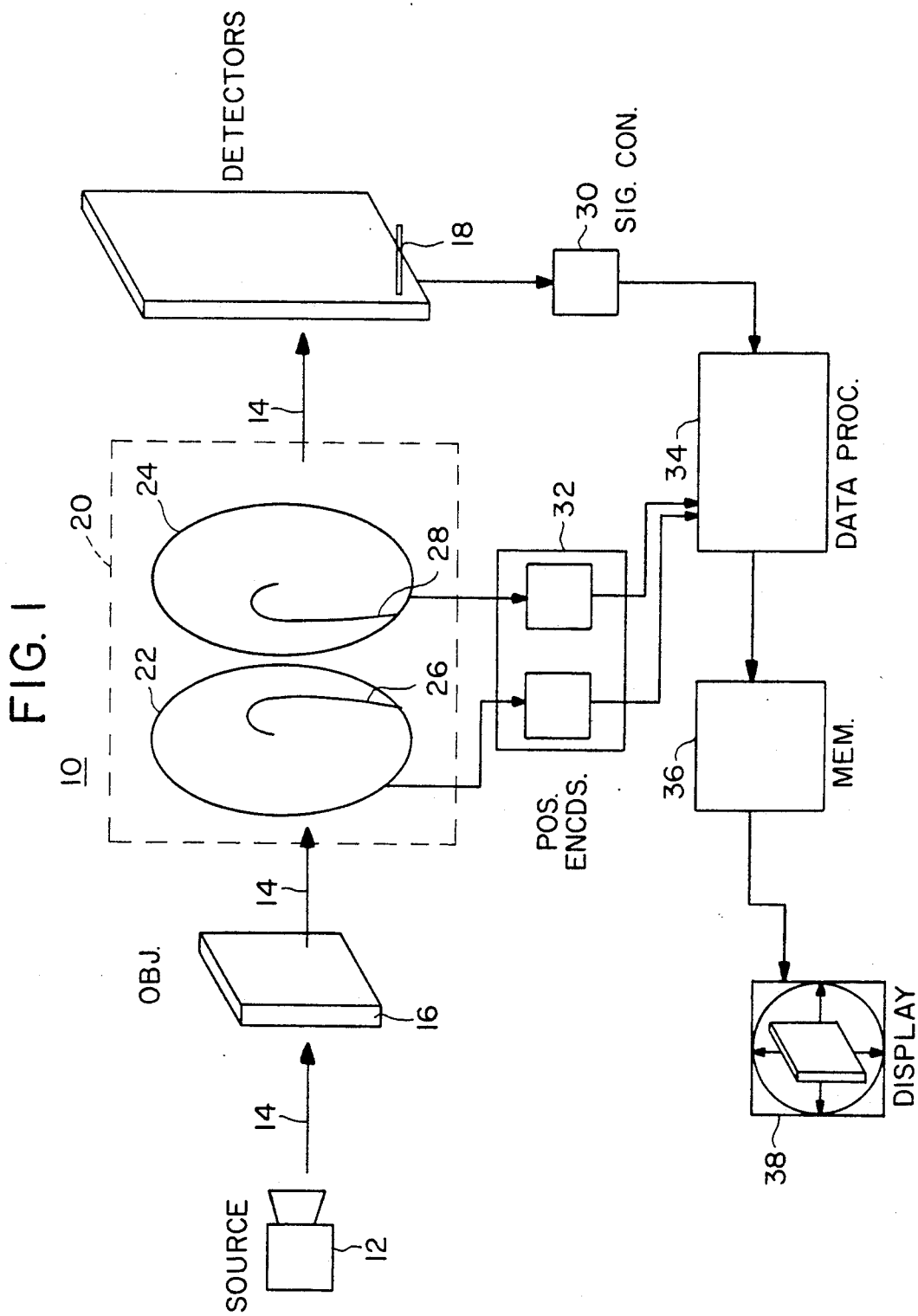
FIG. 1 is a schematic block diagram of a system for radiographically inspecting an object incorporating the teachings of the present invention.
Figure 5:
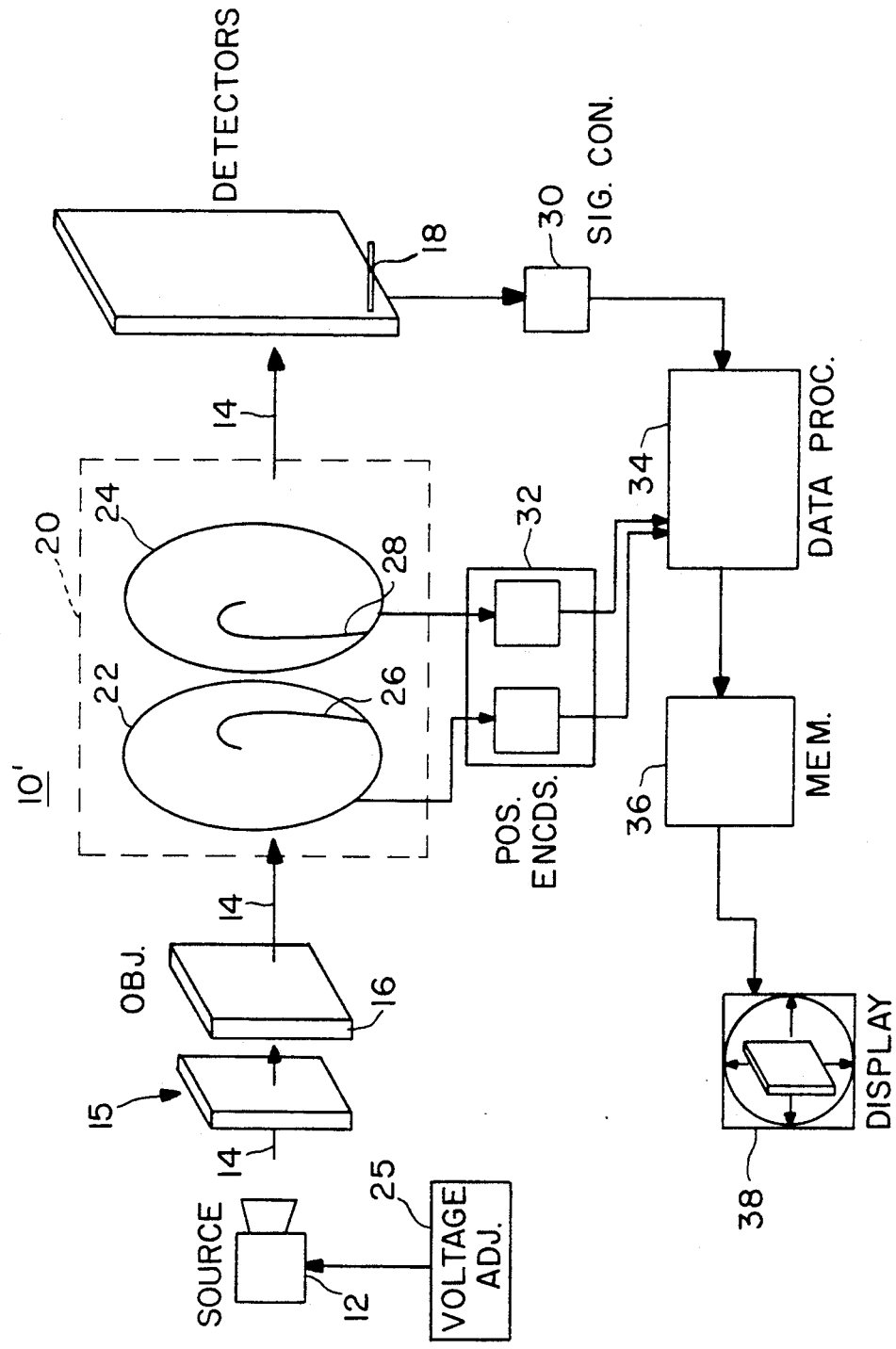
FIG. 5 is a schematic block diagram of the embodiment of the system illustrated in FIG. 1 with the atomic element filtering means included therein in accordance with the present invention.

Preferred embodiments of the system for radiographically inspecting a relatively stationary object are shown in FIGS. 1 and 5 and are generally represented by the numerals 10 and 10' respectively.

These systems include a radiation source 12 which is operative to transmit radiation along a radiation path in a direction, indicated by line 14, toward a selected location. An object 16 is positioned at the selected location. The radiation transmitted by source 12 is in the form of a radiation beam having a cross-sectional area at least corresponding to a predetermined inspection area of the object 16. Radiation source 12 preferably transmits either X-ray or gamma ray radiation of a predetermined energy spectrum. Accordingly, source 12 may be, for example, a 320 KVP X-ray tube and housing available from Siefert X-Ray Corp. of Fairview Village, Pa.

System 10' (FIG. 5) also includes a piece of shielding material 15 that shapes the spectrum of the radiation such that the lower end of the spectrum is more attenuated than the higher end of the spectrum.

Systems 10 and 10' further include detection means 18 having a detection area. The detection area of detection means 18 corresponds to the predetermined inspection area of object 16. That is, the predetermined inspection area of object 16 and the detection area of detection means 18 are of substantially the same size and are aligned in the radiation path. In FIG. 5, the area of shielding or filtering material 15 is the same as the radiation beam area. As here embodied, detection means 18 comprises electronic detectors responsive to radiation to generate response signals. Electronic detectors of the type described above include, for example, plastic scintillator-photomultiplier combination electronic radiation detectors available from Bicron Corp. of Newburg, Ohio, each of which generates electronic signals in response to radiation incident upon a given electronic radiation detector.

As shown in FIG. 1, detection means 18 is disposed relative to radiation source 12 and object 16 such that object 16 is disposed, at the selected location, between source 12 and detection means 18, in the radiation path.

As shown in FIG. 5 filter means 15 is disposed relative to radiation source 12 and object 16 such that filter area 15 is disposed at the selected location between source 12 and object 16.

System 10 or 10' also includes a scanning point selection means 20. As here embodied, scanning point selection means 20 includes a first rotating disk 22 and a second rotating disk 24. Both rotating disks 22 and 24 are formed of a material having a high atomic number such as, for example, lead (atomic no. - 82). First rotating disk is disposed in the radiation path of FIG. 1 and FIG. 5 between radiation source 12 and detecting means 18. Accordingly, the first radiation beam from radiation source 12 is transmitted to first rotating disk 22, the cross-sectional area of the first radiation beam being incident upon first rotating disk 22. First rotating disk 22 includes a spirally-shaped aperture 26. As disk 22 is rotated, aperture 26 of disk 22 operates to sequentially select and transmit spirally-shaped portions of the cross-sectional area of the first radiation beam along the radiation path towards detection means 18. The sequential selection and transmission of spirally-shaped portions of the first radiation beam is performed inasmuch as rotating disk 22 blocks radiation from source 12, except for radiation incident at aperture 26 of disk 22. Rotation of disk 22 is described in detail hereinafter. The shape of aperture 26 of rotating disk 22 is also described in detail hereinafter.

Rotating disk 24 is also disposed in the radiation path. Rotating disk 24 is disposed between rotating disk 22 and detection means 18 in FIG. 1 and FIG. 5 and is preferably aligned with rotating disk 22, such that an imaginary line from source 12 to detection means 18 includes points coincident with the centers of both rotating disks 22 and 24. Planes defining surfaces of the disks are substantially parallel. Rotating disk 24 includes a spirally-shaped aperture 28. As disk 24 is rotated, aperture 28 operates to sequentially select and transmit from the spirally selected portions from disk 22 areas of radiation each corresponding to a pencil beam of radiation. The pencil beam areas of radiation are transmitted along the radiation path to detection means 18. Rotating disk 24 operates to sequentially select and transmit pencil beam areas of radiation by blocking the spirally-shaped portions of radiation from rotating disks 22 except for the radiation incident at the aperture 28.

Rotating disks 22 and 24 are rotated at separate speeds using for example, separate motors and rotating gears (not shown). The rotation of disk 22 is relatively slow in comparison with the rotation of rotating disk 24. Rotating disk 22 is kept stationary during a predetermined time while second rotating disk 24 is rotated through one complete revolution of 360°. The predetermined time period during which the second rotating disk 24 is rotated through a complete revolution may be, for example, 1/30th of a second, but may vary in accordance with the predetermined intensity of radiation from source 12. This predetermined time period may preferably be increased as the intensity of the radiation from source 12 is decreased to provide a larger signal to noise ratio for a weaker source. At the end of the predetermined time, first rotating disk 22 is rotated to a new position.

Rotating disk 22 is rotated through a distance corresponding to the width of aperture 26 of disk 22. As disk 22 and 24 rotate, apertures 26 and 28 are themselves rotated, cooperatively, to permit a single pencil beam of radiation to pass from radiation source 12 to detection means 18 in the manner described above. That is, as aperture 26 of rotating disk 22 is rotated to permit spirally-shaped portions of the radiation beam from source 22 to be sequentially transmitted to rotating disk 24, aperture 28 is rotated in a manner such that alignment exists for only a single point from each of apertures 26 and 28. The alignment which exists between points of apertures 26 and 28 is further described below.

Preferably, the spirally-shaped apertures 26 and 28 of disks 22 and 24, respectively, are shaped in the form of spiral curves. The spiral curves may have a variety of specific shapes such as parabolic, linear (Archimedian) quadradic or logarithmic (equiangular). Referring to FIG. 2, three specific, exemplary, shapes for corresponding spiral curves for rotating disks 22 and 24 are shown. Also shown are equations for the corresponding spiral curves of rotating disks 22 and 24.

Equations in polar coordinates for curved aperture 26 of disk 22 are given below.

$$R_1 = a \times \sqrt{\theta} \text{ (parabolic spiral)} \tag{1}$$

$$R_1 = a \times \theta \text{ (spiral or Archimedes)} \tag{2}$$

$$R_1 = a \times \theta^2 \text{ (quadradic spiral)} \tag{3}$$

In the foregoing equations, a represents a constant, $\theta$ represents the polar angle in radian measure from a horizontal axis, and $R_1$ denotes the radius vector of disk 22. Corresponding equations for curved aperture 28 of disk 24 are given below.

$$R_2 = a \times \sqrt{(\pi - \theta)} \quad (4)$$

$$R_2 = a \times (\pi - \theta) \quad (5)$$

$$R_2 = a \times (\pi - \theta)^2 \quad (6)$$

In equations (4), (5) and (6) which respectively correspond to equations (1), (2) and (3), a represents a constant, $\theta$ represents the polar angle in radian measure from the horizontal axis, and $R_2$ denotes the radius vector of disk 24.

The width of both apertures 26 and 28 is preferably between 0.1 and 1.00 millimeters.

Figure 3C:
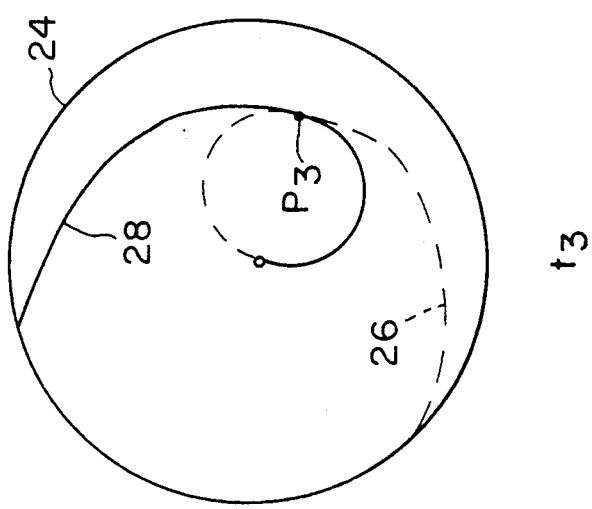
FIGS. 3A, 3B and 3C are a cross-sectional diagrams of the rotating disks showing the relative position of respective spiral slits during rotation.
Figure 3B:
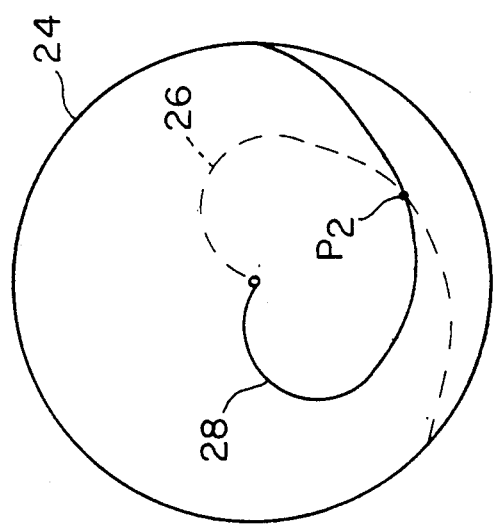
Figure 3A:
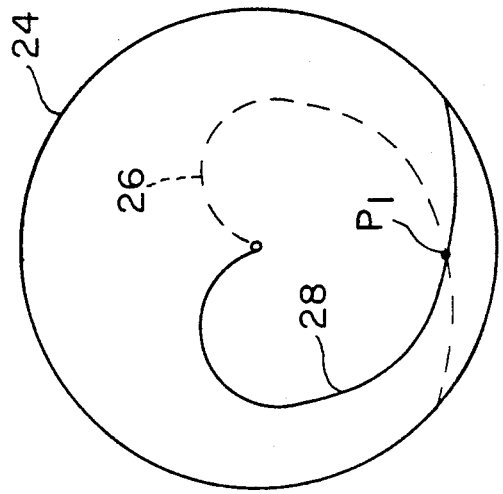

In FIGS. 3A, 3B and 3C, the manner in which apertures 26 and 28 are aligned to selectively transmit pencil beams of radiation is depicted. Curved apertures 26 and 28 are shown, superimposed cross-sectionally at times $t_1$, $t_2$ and $t_3$. The time between times $t_1$, $t_2$ and $t_3$ is less than a predetermined time period for rotating second disk 24 through a complete revolution. Accordingly, aperture 26 of disk 22 is shown in the same position during each of times $t_1$, $t_2$ and $t_3$. On the other hand, aperture 28 of disk 24 is shown in different positions corresponding to positions assumed by aperture 28 during rotation. At each time $t_1$, $t_2$ and $t_3$ points of cross-sectional alignment of aperture 26 and 28 exist at cross-sectional points $P_1$, $P_2$ and $P_3$, respectively. These points indicate the location of pencil beams of radiation from source 12 passing through both rotating disks. As aperture 28 rotates, aperture 28 sequentially selects and transmits pencil beams of radiation, from points as shown, to individual point-area portions of the detection area of detection means 18 in system 10 of FIG. 1 and through filter member 15 to detection means 18 of FIG. 5. With the rotation of disk 22, points of alignment for the disks are moved and pencil beams of radiation are sequentially selected and transmitted by disk 24 to the remaining portions of the detection area of detection means 18, the sequential selection and transmission resulting in a spiral sweep of point area portions of detection means 18.

Since, as described above in connection with the embodiments of FIG. 1 and FIG. 5, the selected location where the object is positioned is located between source 12 and detection means 18, in the radiation path, the first radiation beam from source 12 is incident upon object 16 or through filter 15 (FIG. 5) and incident upon 16. After interaction with object 16, radiation reaches scanning point selection means 20, and is sequentially transmitted in pencil beam form to detection means 18.

Radiation from source 12 incident upon object 16, interacts with object 16 resulting in the production of compton scattered gamma rays, total photoelectric absorption of incident radiation, and production of gamma ray photon pairs at photon energies sufficient to cause radiation to pass through and emerge from object 16. The above-described interactions are unique to and representative of object 16. Accordingly, radiation emerging from object 16 and reaching detection means 18 is characteristic of object 16, or characteristic of the elements constituting object 16, as are the signals generated in response to the radiation reaching detection means 18. These signals are used to obtain an image of the inspection area of object 16.

With more particular reference to the system of FIG. 5, generally referred to as 10' wherein like reference numerals refer to like elements, filtering means 15 is disposed between radiation source 12 and object 16. Filtering means 15 is preferably in the form of a plate of a selected thickness that has an area corresponding at least to the area of the radiation beam. Filtering means 15 may be made from different elements that attenuate the X-ray source. Depending upon the element used, the X-ray spectrum will be shaped such that the lower end of the spectrum will be attenuated more than the higher end of the spectrum. This will provide a narrow energy spectrum that will cause X-ray fluorescents from only those elements that have K and L shells within the energy band. Further, the X-ray spectra will not only be varied by filtering the spectra with different elements, but will also be varied by changing the energy of X-ray source 12 by conventional means referred to in block 25. All of the interactions via the photoelectric process result in the emission of fluorescent photons. Thus, the amount of radiation emitted from object 16 depends on the amount of radiation in the spectra at the atomic energy levels for the element of interest.

Figure 7:
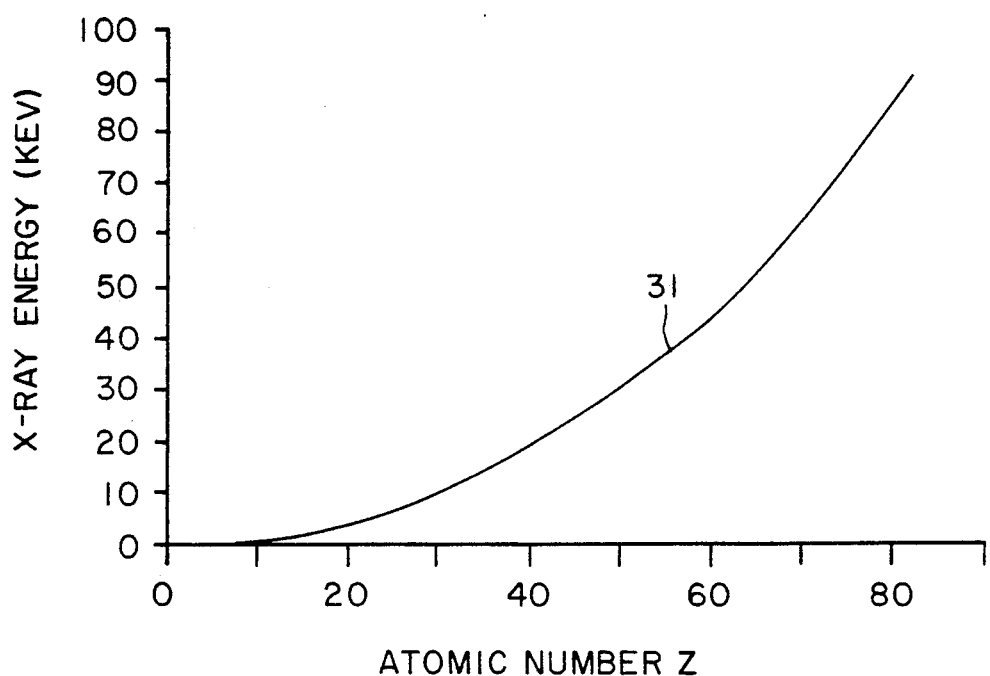
FIG. 7 is a graphical representation of X-ray fluorescent energy as a function of the atomic element number.

As an electron is ejected from its energy shell, another electron fills its position with the emission of a fluorescent photon. With reference to FIG. 7, curve 31 represents the energy of the fluorescent photons as a function of the atomic number Z of the object 16. The X-ray absorption energies for the individual elements is well known. A table of such energies may be found in the CRC Handbook published by The Chemical Rubber Company, 45th Edition pages E72-E75 thereof and the Review of Scientific Instruments, Volume 23, Nos. 10, at page 523, published in 1952. To excite the various elements requires photons in the primary beam from source 12 at the energy levels of interest. The amount of fluorescent photons given off from an element is directly proportional to the photons in the spectrum at that particular energy level.

Figure 8:
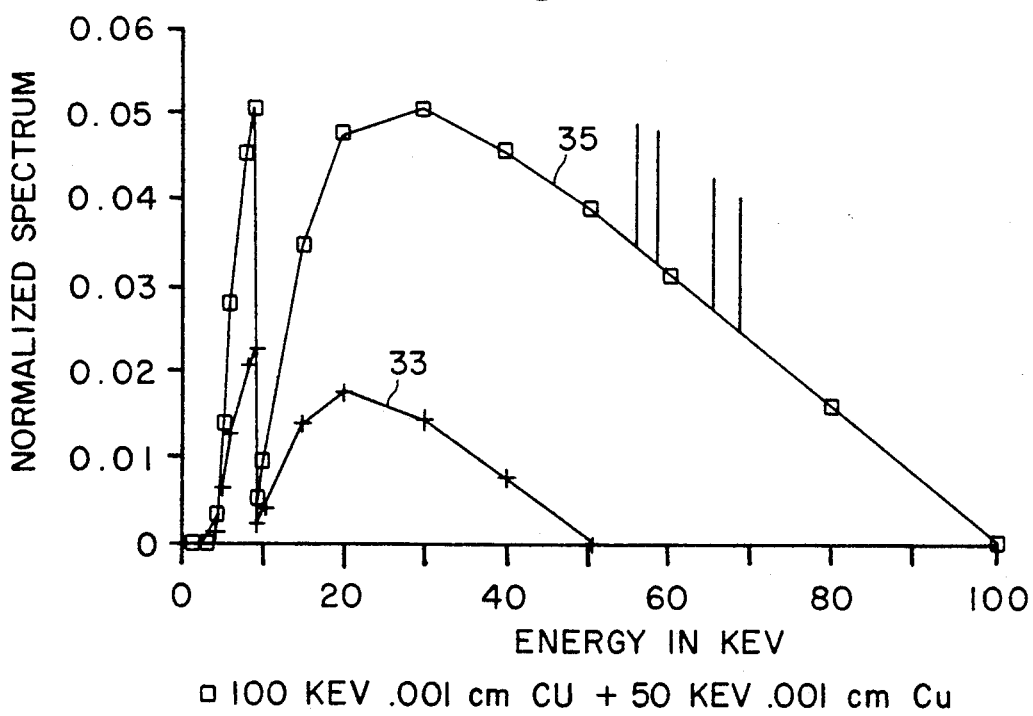
FIG. 8 is a graphic illustration of the effects of X-ray tube voltage on the transmitted X-ray spectrum.
Figure 9:
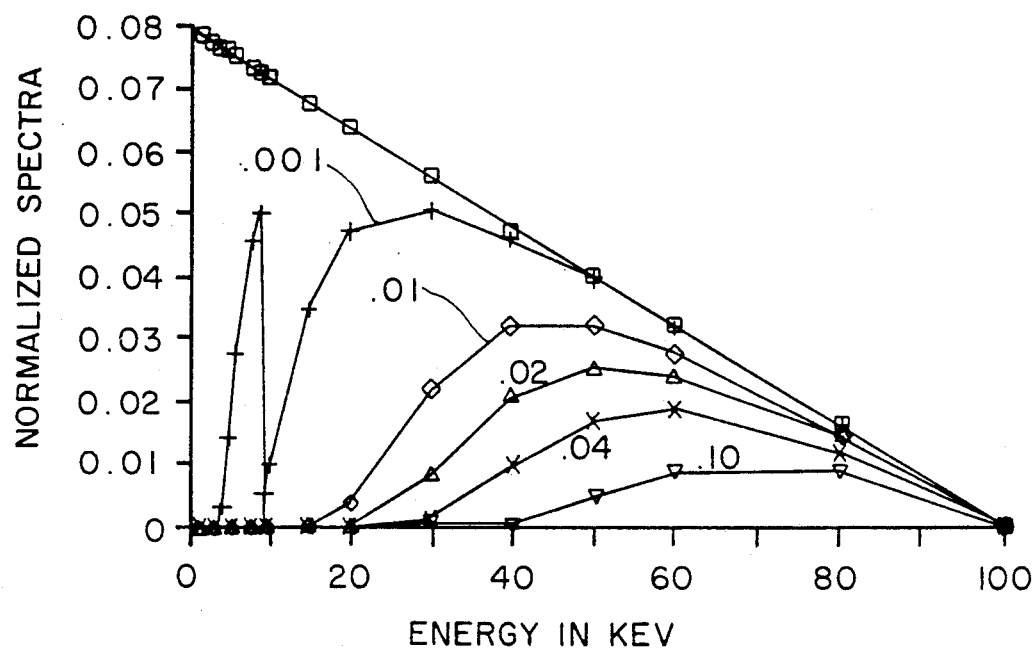
FIG. 9 is a graphical representation of the effect of copper filters at 100 KEV on the X-ray energy spectrum.

Referring to FIG. 8, the X-ray spectra for tungsten from an X-ray tube is illustrated for two different energies by curves 33 and 35, respectively. Curve 33 represents a maximum voltage of 50 KEV, and curve 35 a maximum voltage of 100 KEV. The spectra contains photons up to the maximum voltage applied to the X-ray tube. They contain a continuous distribution of photons plus fluorescent radiation characteristic of the X-ray target element. The spectra 33 and 35 can be modified by absorbing a portion of the spectra using various elements of various thickness as shown by the curves in FIG. 9 for the element copper. An unlimited number of combinations of energy and filters may be utilized to shape the beam.

Figure 10:
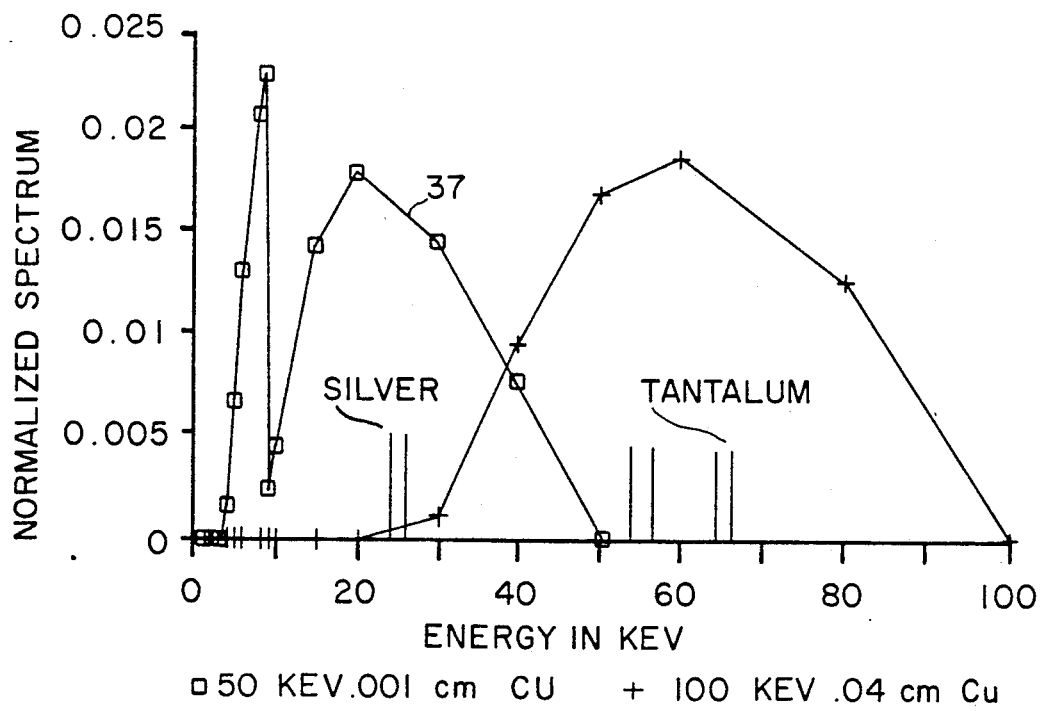
FIG. 10 is a graphic illustration of the effect of voltages for different copper filter thicknesses on the transmitted X-ray spectrum of different peak voltage.

With reference to FIG. 10, curves 37 and 39 represent the imaging of silver and tantalum, respectively. With respect to silver, the X-ray beam is generated using a 50 KEV source with light filtration of 0.001 cm. of copper. Only the element silver will show up of in the scanning image object 16 at 50 KEV. In the event the X-ray potential is increased to 100 KEV and 0.04 cm. of copper is applied to filter out the lower portion of the spectrum as shown in FIG. 10, the major source of fluorescent radiation will now come from the tantalum and show up in the scanning image.

Referring again to FIGS. 1 and 5, systems 10 and 10' further include a signal conditioning means. As here embodied, the signal conditioning means comprises an analog to digital converter 30 responsive to detection means 18 for converting the analog signals generated by detection means 18 to digital form. Analog to digital converter 30 may be, for example, a model 7612D analog to digital converter available from Tektronix, Inc. of Beaverton, Oreg., which converts received analog signals into digital signals.

Systems 10 and 10' further include position encoder means 32. As here embodied, the position encoder means 32 includes means for determining the position of each selected portion of the first radiation beam. That is, position encoder means 32 is responsive to scanning point selection means 20 to determine the point of alignment between disk 22 and 24 to obtain the location of the portion of the first radiation beam transmitted from source 12 through object 16 to detection means 18 at any given time. Position encoder 30 may comprise, for example, means for sensing edge markings on each of disks 26 and 28, and for utilizing information as to the mathematical relationship between the edge marking for each disk and the location of the spiral aperture for the disk relative to the markings. This exemplary position encoder would also comprise a photodetector for receiving light reflections from disk edge markings to determine the present rotational position of a disk.

A data processing means of the systems is responsive to position encoder means 32 and detection means 18 for processing the signals generated by detection means 18. As here embodied, the processing means comprises a data processor 34 which establishes a correspondence between a portion of object 16 through which the first radiation beam passes to detection means 18 and response signals generated as radiation is passed through the portion of object 16. Response signals for each pencil beam portion of the detection area of detection means 18 are obtained and processed by data processor 34.

Systems 10 and 10' also include an image memory 36 responsive to data processor 34 for storing the signals processed by processor 34, and a display means governed by data processor 34 for generating a radiographic image of the inspection area of object 16 in accordance with the signals stored by image memory 36. Image memory 36 may be, for example, a model ST-100 memory device available from Star Technologies, Inc. of Sterling, Va. The display means, here embodied as display means 38, and which may be, for example, a model NEC Multisync, monitor available from NEC Home Electronics, Inc. of Wood Dale, Ill., provides a visual display of an image of object 16.

Figure 4:
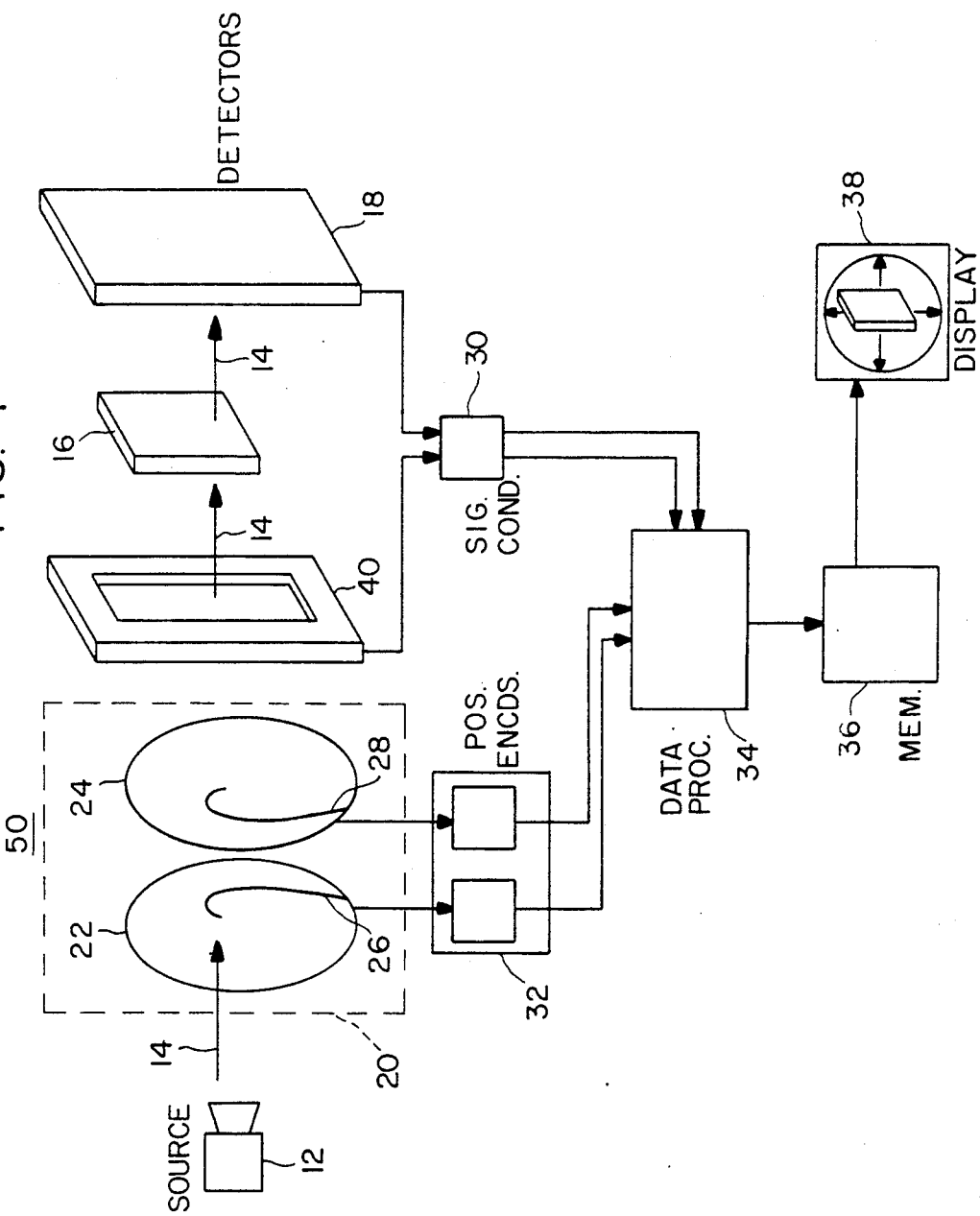
FIG. 4 is a block diagram of a system for radiographically incorporating the teaching of the present invention in accordance with another embodiment thereof.
Figure 6:
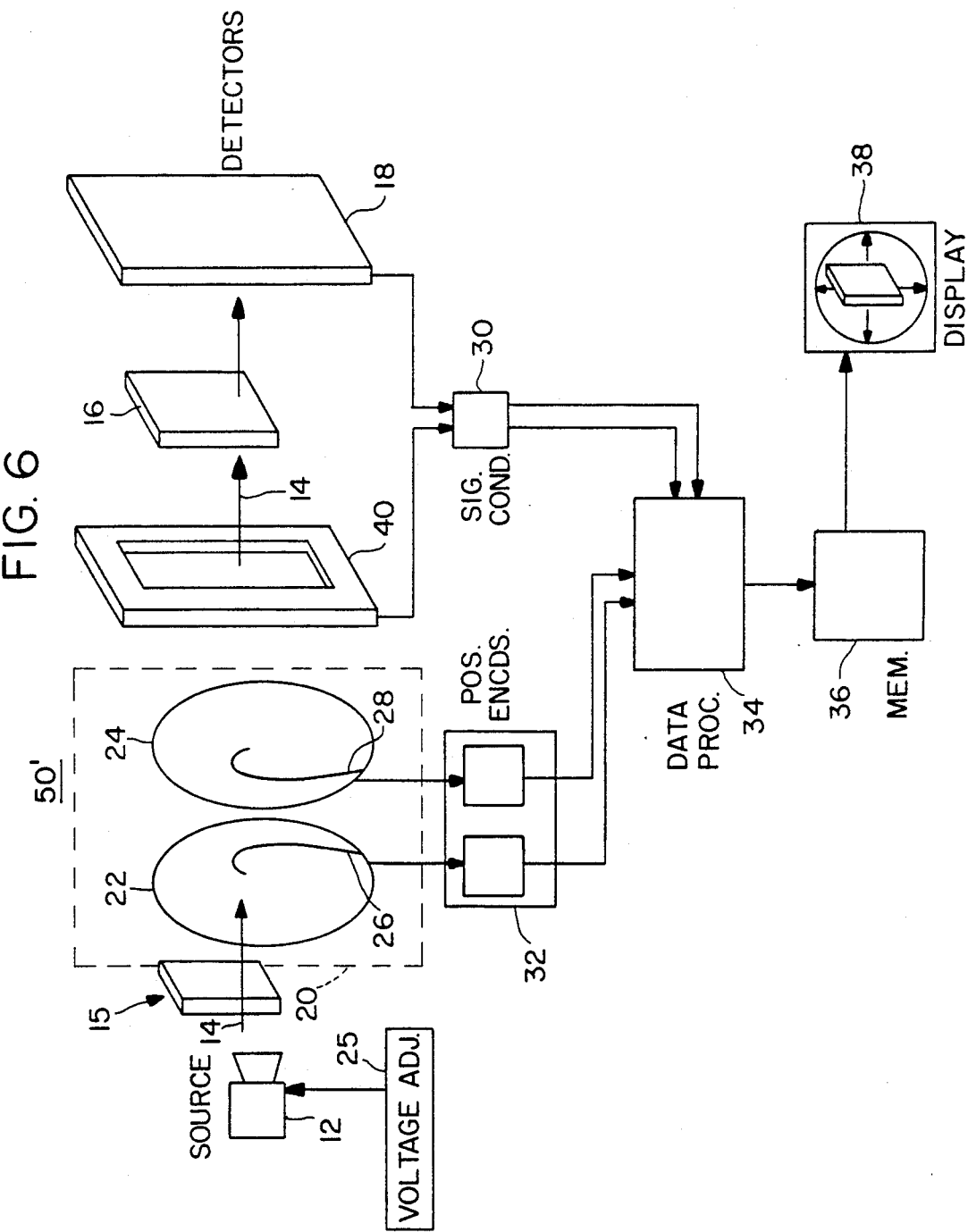
FIG. 6 is a schematic block diagram of the embodiment of the system illustrated in FIG. 4 with the atomic element filtering means included therein in accordance with the present invention.

Referring to FIGS. 4 and 6, the preferred embodiments 50 and 50' of the systems of the present invention are described. In FIG. 4, a system 50 having apparatus and a manner of operation substantially similar to the apparatus and manner of operation of system 10, is shown. In FIG. 6, a system 50' having apparatus and a manner of operation similar to system 10'. Accordingly, the apparatus of systems 50 and 50' are shown with like reference numerals. Since systems 10 and 50, and 10' and 50' are substantially similar, only the differences between such systems are set forth below.

In system 50 and system 50', the selected location at which object 16 is positioned is located in the radiation path between scanning point selection means 20 and detection means 18. In connection with the location of object 16 between scanning point selection means 20 and detection means 18, systems 50 and 50' each further comprise a backscatter detection means 40. Backscatter detection means 40 detects radiation interactive with and backscattered by object 16, that is, radiation traveling "backward" from object 16 as a result of either compton scattering or photoelectric fluorescence, and generates signals in response to the radiation detected. Data processor 34 is responsive to the response signals generated by backscatter detection means 40 to process the response signals as described above.

An image obtained using both backscatter and through radiation more fully reveals the interactions undergone by object 16 and thus such an image provides a truer representation of the object or the classification of elements in the object. Accordingly, in instances where it is not otherwise undesirable to utilize backscatter detection means 40, the radiographic inspection system of the present invention may include such means. In fact, where for some reason use of detection means 18 proves impractical, only backscatter detection mean 40 may be used in obtaining an image of object 16.

With the rotation of disks 22 and 24, as described above, it may occur that an area of detection means 18 and/or 40 detects radiation from a pencil beam of radiation transmitted through scanning point selection means 20 that does not have a uniform cross-section at each point on object 16. This happens in cases where the areas for aperture intersection points vary in size or when the radiation from unit 20 is not uniform in intensity. To compensate for such non-uniformity, data processor 34 corrects the data obtained for image 16 using data obtained from a field flattening scan. Using a uniform calibration object for object 16, spatial variation inspection data is stored in the data memory in a calibration file that will be used to correct all other inspection data.

Also, as described above, disks 22 and 24 are rotated by gears. These gears support disks 22 and 24 at their edges, so that no "dead spots" occur in the center.

In view of the foregoing, it should be understood that in addition to disclosure of an improved system for radiographically inspecting a relatively stationary object, a related method for doing the same has been disclosed. The method comprises the steps of: transmitting a first radiation beam having a cross-sectional area at least corresponding to the predetermined inspection area along a radiation path in a direction toward the selected location; selecting, sequentially, portions from the cross-sectional area of the first radiation beam and transmitting the selected portions along the radiation path to the selected location, each said selected portion of the cross-sectional area of the first radiation beam comprising a pencil beam of radiation; detecting each of the selected portions of the first radiation beam striking corresponding portions of the predetermined inspection area of an object at the selected locations and generating signals in response to the radiation stiking the corresponding portions; determining the position of each selected portion of the first radiation beam; processing the signals generated in response to the radiation striking the corresponding portions; and generating a radiographic image of the predetermined area of the object.

In another aspect the method further comprises the step of filtering each selected portion of the first radiation beam into at least a selected atomic element group for generating a radiographic image of the predetermined area of the object.

It should be apparent to those skilled in the art that various modifications may be made to the improved system and method for radiographically inspecting a relatively stationary object without departing from the scope or spirit of the invention. Thus, it is intended that the invention cover modifications and variations of the invention, provided they come within the scope of the appended claims and their legally entitled equivalents.

I claim:

1. A system for radiographically inspecting a predetermined area of relatively stationary object positioned at a selected location, comprising:

a source of radiation operative to transmit along a radiation path toward the selected location a fixed position radiation beam having a cross-sectional area at least corresponding to the predetermined inspection area;

detection means, having a detection area at least corresponding to the predetermined inspection area disposed in a fixed position in the radiation path in alignment with the fixed position radiation beam;

scanning point selection means, disposed in the radiation path between the radiation source and detection means, for sequentially selecting and transmitting a plurality of selected portions of the cross-sectional area of the fixed position radiation beam striking in sequence a corresponding plurality of portions of the detection area of the detection means in both the length and width dimension, each said selected portion of the cross-sectional area of the fixed position radiation beam corresponding to a pencil beam of radiation, the selected plurality of portions of the cross-sectional area of the radiation beam and the corresponding portions of the detection means, each having both a width dimension and a length dimension substantially greater than the cross-sectional area of each pencil beat at the selected location, said detection means being responsive to each said selected portion of the fixed position radiation beam striking a corresponding portion of the detecting area for generating signals corresponding to radiation interactive with a corresponding portion of the predetermined inspection area of an object at the selected location;

position encoder means responsive to said scanning point selection means for determining the position of each selected portion of the fixed position radiation beam;

data processing means responsive to said position encoder means and said detecting means for processing the signals generated by the detected means; and display means governed by said data processing means for generating a radiographic image of the predetermined area of the object.

2. The system of claim 1 further comprising filtering means fixedly disposed in the radiation path between the radiation source and the scanning point selection means for determining the identity of at least a grouping of atomic elements.

3. The system of claim 1 wherein the scanning point selection means comprises:

a first rotating disk having a spirally-shaped aperture, disposed in the radiation path between the radiation source and the detection means, for sequentially selecting and transmitting spirally-shaped portions of the cross-sectional area of the fixed position radiation beam along the path in the direction toward the selected location; and a second rotating disk having an opposite spirally-shaped aperture, disposed in the radiation path in alignment with said first rotating disk between said first rotating disk and the detecting means, for sequentially selecting from said spirally-shaped portions, and for transmitting to the selected location, said selected portions of cross-sectional area each corresponding to a said pencil beam of radiation.

4. The system of claim 2 wherein the filtering means comprises a fixed member composed of a selected atomic element having an area corresponding to at least the total radiation beam area; and means for selecting the intensity of the radiation source in accordance with the selected element.

5. The system of claim 3, wherein said detection means includes a detection device wherein said radiation source and the detection device are disposed with the selected location therebetween.

6. The system of claim 3, wherein said detection means includes a defection device disposed in the radiation path between said radiation source and the selected location.

7. The system, of claim 3, wherein said detection means comprises a first detector device and a second detector device responsive to each of the selected portions of the fixed position radiation beam, said first detector device being positioned such that said first detector device and said radiation source are disposed with the selected location therebetween, said second detector device being disposed between said radiation source and the selected location.

8. The system of claim 4 wherein the scanning point selection means comprises:

a first rotating disk having a spirally-shaped aperture, disposed in the radiation path between the radiation source and the detection means, for sequentially selecting and transmitting spirally-shaped portions of the cross-sectional area of the fixed position radiation beam along the path in the direction toward the selected location; and a second rotating disk having an opposite spirally-shaped aperture, disposed in the radiation path in alignment with said first rotating disk between said first rotating disk and the detecting means, for sequentially selecting from said spirally-shaped portions, and for transmitting to the selected location, said selected portions of cross-sectional area each corresponding to a said pencil beam of radiation.

9. The system of claim 7, further comprising filtering means for determining the identity of at least a grouping of atomic elements disposed between the radiation source and selected location second detection device.

10. The system of claim 8, wherein said first and second rotating disks are comprised of a material having a high atomic number, and wherein said spirally-shaped apertures of said first and second rotating disks are shaped in the form of spiral parabolic curves respectively represented by the equations in polar coordinates:

$$R_1 = a \times \sqrt{\theta}, \text{ and}$$

-continued $$R_2 = a \times \sqrt{(\pi - \theta)},$$

where a represents a constant, $\theta$ represents the polar angle in radian measure from the horizontal axis, and $R_1$ and $R_2$ represent the radius vector of disks, the first and second, rotating respectively.

11. The system of claim 3, wherein said first and second rotating disks are comprised of a material having a high atomic number, and wherein said spirally-shaped apertures of said first and second rotating disks are shaped in the form of spiral Archimedian curves respectively represented by the equations in polar coordinates:

$$R_1 = a \times \theta, \text{ and}$$

$$R_2 = a \times (\pi - \theta),$$

where a represents a constant, $\theta$ represents the polar angle in radian measure from the horizontal axis, and $R_1$ and $R_2$ represent the radius vectors of disks, the first and second rotating respectively.

12. The system of claim 8 wherein said first and second rotating disk are comprised of a material having a high atomic number, and wherein said spirally-shaped apertures of said first and second rotating disks are shaped in the form of spiral Archimedian curves respectively represented by the equations in polar coordinates:

$$R_1 = a \times \theta, \text{ and}$$

$$R_2 = a \times (\pi - \theta),$$

where a represents a constant, $\theta$ represents the polar angle in radian measure from the horizontal axis, and $R_1$ and $R_2$ represent the radius vectors of disks 22 and 24, respectively.

13. The system of claim 3, wherein said first and second rotating disks are comprised of a material having a high atomic number, and wherein said spirally-shaped apertures of said first and second rotating disks are shaped in the form of spiral quadradic curves respectively represented by the equations in polar coordinates:

$$R_1 = a \times \theta^2, \text{ and}$$

$$R_2 = a \times (\pi - \theta)^2,$$

where a represents a constant, $\theta$ represents the polar angle in radian measure from the horizontal axis, and $R_1$ and $R_2$ represent the radius vectors of disks 22 and 24, respectively.

14. The system of claim 8 wherein said first and second rotating disks are comprised of a material having a high atomic number, and wherein said spirally-shaped apertures of said first and second rotating disks are shaped in the form of spiral quadradic curves respectively represented by the equations in polar coordinates:

$$R_1 = a \times \theta^2, \text{ and}$$

$$R_2 = a \times (\pi - \theta)^2,$$

where a represents a constant, $\theta$ represents the polar angle in radian measure from the horizontal axis, and $R_1$ and $R_2$ represent the radius vectors of disks 22 and 24, respectively.

15. The system of claim 3, wherein the system further comprises an image memory, responsive to said data processing means, for storing the signals processed by said data processing means, said display means being responsive to the signals stored by said image memory to generate the radiographic image of the predetermined area of the object.

16. The system of claim 8 wherein the system further comprises an image memory, responsive to said data processing means, for storing the signals processed by said data processing means, said display means being responsive to the signals stored by said image memory to generate the radiographic image of the predetermined area of the object.

17. A method for radiographically inspecting a predetermined area of relatively stationary object positioned at a selected location comprising the steps of:
transmitting a fixed position radiation beam having a cross-sectional area at least corresponding to the predetermined inspection area along a radiation path in a direction toward the selected location;
selecting sequentially a plurality of portions from the cross-sectional area of the fixed position radiation beam and transmitting the selected portions along the radiation path to the selected location, each said selected portion of the cross-sectional area of the fixed position radiation beam corresponding to a pencil beam of radiation, said plurality of portions having both a length and width dimension substantially greater than the cross-sectional area of each pencil beam;
detecting each of the selected portions of the fixed position radiation beam striking corresponding portions of the predetermined inspection area of an object at the plurality of selected locations and generating signals in response to the radiation striking the corresponding portions said plurality of locations having both a length and width dimensions substantially greater than the cross-sectional area of each pencil beam;
determining the position of each selected portion of the fixed position radiation beam;
processing the signals generated in response to the radiation striking the corresponding portions; and
generating a radiographic image of the predetermined area of the object.

18. The method of claim 17 wherein the step of sequentially selecting and transmitting the portions from the cross-sectional area of the first radiation beam comprises the substeps of:
sequentially selecting and transmitting selected spirally-shaped portions of the cross-sectional area of the fixed position radiation beam along the radiation path in the direction toward the selected location; and
sequentially selecting from said spirally-shaped portions, and transmitting to the selected location portions of cross-sectional area each corresponding to a said pencil beam of radiation.

19. The method of claim 17 wherein the method further comprises the step of storing the processed signals for generating a radiographic image of the predetermined area of the object.

20. A system for radiographically inspecting a predetermined area of a relatively stationary object positioned at a selected location, comprising:
a source of radiation operative to transmit along a radiation path, toward the selected location, a fixed radiation beam of a selected energy intensity having a cross-sectional area at least corresponding to the predetermined inspection area;

detection means, having a detection area at least corresponding to the predetermined inspection area, disposed in the radiation path in alignment with the fixed radiation beam;

scanning point selection means including a first rotatable disk having a spirally-shaped aperture, disposed in the radiation path between the radiation source and the detection means, said disk being rotatable a distance corresponding to a width of the aperture at the end of a predetermined time period for sequentially selecting and transmitting spirally-shaped portions of the cross-sectional area of the fixed radiation beam along the path in the direction toward the selected locations; and a second rotatable disk having an opposite spirally-shaped aperture disposed in the radiation path in alignment with said first rotatable disk between said first rotatable disk and the detection means, and being completely rotatable during the predetermined time period for sequentially selecting from said spirally-shaped portions and for transmitting to the selected location, said selected portions of cross-sectional area each corresponding to a said pencil beam of radiation, said time period being pre-selected in accordance with the selected energy intensity;

said detection means being responsive to each said selected portion of the fixed radiation beam striking a corresponding portion of the detecting area for generating signals corresponding to radiation interactive with a corresponding portion of the predetermined inspection area of an object at the selected location;

position encoder means responsive to said scanning point selected means for determining the position of each selected portion of the fixed radiation beam;

data processing means responsive to said position encoder means and said detection means for processing the signals generated by the detection means; and display means governed by said data processing means for generating a radiographic image of the predetermined area of the object.

21. The system of claim 20 further comprising filtering means disposed in the radiation path between the radiation source and the detection means for determining the identity of at least a grouping of atomic elements, and wherein the filtering means includes a member composed of a selected atomic element having an area corresponding to at least the radiation beam area; and means for selecting the intensity of the radiation source in accordance with the selected element.

22. A system for radiographically inspecting a predetermined area of a relatively stationary object positioned at a selected location, comprising:

a source of radiation operative to transmit along a radiation path, toward the selected location, a fixed radiation beam having a cross-sectional area at least corresponding to the predetermined inspection area;

detection means, having a detection area at least corresponding to the predetermined inspection area, disposed in the radiation path in alignment with the fixed radiation beam;

scanning point selection means including a first disk having an elongate aperture, disposed in the radiation path between the radiation source and detection means, said first disk being rotatable at the end of a predetermined time period, a distance corresponding to a width of the elongate aperture, and a second disk having an elongate aperture with a predetermined orientation relative to the first disk, said second disk being rotatable completely during the predetermined time period, for sequentially selecting and transmitting selected portions of the cross-section area of the fixed radiation beam striking in sequence corresponding portions of the detection area of the detection means, each said selected portion of the cross-section area of the fixed radiation beam corresponding to a pencil beam of radiation, said detection means being responsive to each said selected portion of the first radiation beam striking a corresponding portion of the detecting area for generating signals corresponding to radiation interactive with a corresponding portion of the predetermined inspection area of an object at the selected location;

position encoder means responsive to said scanning point selection means for determining the position of each selected portion of the first radiation beam;

data processing means responsive to said position encoder means and said detection means for processing the signals generated by the detection means; and display means governed by said data processing means for generating a radiographic image of the predetermined area of the object.

23. The system of claim 22, further comprising filtering means disposed in the radiation path between the radiation source and the detection means for determining the identity of at least a grouping of atomic elements; and wherein the filtering means includes a member composed of a selected atomic element having an area corresponding to at least the radiation beam area.

24. The system of claim 22 further comprising filtering means disposed in the radiation path between the radiation source and the detection means for determining the identity of at least a grouping of atomic elements.

25. The system of claim 24 wherein the filtering means comprises a member composed of a selected atomic element having an area corresponding to at least the radiation beam area; and means for selecting the intensity of the radiation source in accordance with the selected element.

26. The system of claim 22 wherein said first and second disks are comprised of a material having a high atomic number, and wherein said apertures of said first and second disks are shaped in the form of spiral parabolic curves respectively represented by the equations in polar coordinates:

$$R_1 = a \times 0, \text{ and}$$

$$R_2 = a \times (\pi - 0),$$

where a represents a constant, 0 represents the polar angle in radian measure from the horizontal axis, and $R_1$ and $R_2$ represent the radium vector of disks, the first and second, rotating respectively.

27. The system of claim 22 wherein said first and second disk are comprised of a material having a high atomic number, and wherein said aperture of said first and second rotating disks are shaped in the form of spiral Archimedian curves respectively represented by the equations in polar coordinates:

$$R_1 = a \times 0, \text{ and}$$

$$R_2 = a \times (\pi - 0),$$

where a represents a constant, 0 represents the polar angle in radian measure from the horizontal axis, and $R_1$ and $R_2$ represent the radius vectors of disks, the first and second rotating respectively.

28. The system of claim 24 wherein said first and second disks are comprised of a material having a high atomic number, and wherein said apertures of said first and second rotating disks are shaped in the form of spiral Archimedian curves respectively represented by the equations in polar coordinates:

$$R_1 = a \times 0, \text{ and}$$

$$R_2 = a \times (\pi - 0),$$

where a represents a constant, 0 represents the polar angle in radian measure from the horizontal axis, and $R_1$ and $R_2$ represent the radius vectors of disks 22 and 24, respectively.

29. The system of claim 22 wherein said first and second rotating disks are comprised of a material having a high atomic number, and wherein said spirally-shaped apertures of said first and second rotating disks are shaped in the form of spiral quadradic curves respectively represented by the equation in polar coordinates:

$$R_1 = a \times 0^2, \text{ and}$$

$$R_2 = a \times (\pi - 0)^2,$$

where a represents a constant, 0 represents the polar angle in radian measure from the horizontal axis, and $R_1$ and $R_2$ represent the radius vectors of disks 22 and 24, respectively.

30. The system of claim 24 wherein said first and second rotating disks are comprised of a material having a high atomic number, and wherein said spirally-shaped apertures of said first and second rotating disks are shaped in the form of spiral quadradic curves respectively represented by the equations in polar coordinates:

$$R_1 = a \times 0^2, \text{ and}$$

$$R_2 = a \times (\pi - 0)^2,$$

where a represents a constant, 0 represents the polar angle in radian measure from the horizontal axis, and $R_1$ $R_2$ represent the radius vectors of disks 22 and 24, respectively.

31. The system of claim 22, wherein the system further comprises an image memory, responsive to said data processing means, for storing the signals processed by said data processing means, said display means being responsive to the signals stored by said image memory to generate the radiographic image of the predetermined area of the object.

32. The system of claim 24 wherein the system further comprises an image memory, responsive to said data processing means, for storing the signals processed by said data processing means, said display means being responsive to the signals stored by said image memory to generate the radiographic image of the predetermined area of the object.

33. The system of claim 22, wherein said radiation source includes means operative to transmit radiation of a selected energy intensity, and wherein said first disk is rotatable a distance corresponding to a width of the aperture at the end of a predetermined time period, and said second disk is rotatable completely during a predetermined time period, said time period being preselected in accordance with the selected energy intensity.

34. The system of claim 33 wherein the energy intensity is selected in accordance with the selected element.

35. A method for radiographically inspecting a predetermined area of a relatively stationary object, disposed at a selected location along a radiation path, comprising the steps of:
   transmitting a radiation beam along a radiation path in a first direction toward the selected inspecting location, the beam having a cross-sectional area corresponding at least to the predetermined area of the inspecting location;
   sequentially selecting a plurality of portions of the cross-sectional area of beam of radiation and transmitting the selected portions to the selected location, each said selected portion of the cross-sectional area of the fixed radiation beam corresponding to a pencil beam of radiation, and the plurality of portions of the cross-sectional area of the radiation beam having both a length and width dimension substantially greater than the pencil beam;
   backscattering radiation in a second direction along the radiation path, opposite the first direction, through the object at the selected location;
   detecting each of the plurality of selected portions of the first radiation travelling through an object at the inspecting location and backscattered in the second direction, and detecting second radiation interacting with the object and backscattered in the second direction, the plurality of portions of the inspection area having both a length and width dimension greater than one pencil beam;
   generating signals in response to the detected radiation; and
   processing the response signals for the sequentially selected area portions of the inspecting location to obtain a radiographic representation of the object at the inspecting location.

* * * * *

UNITED STATES PATENT AND TRADEMARK OFFICE
CERTIFICATE OF CORRECTION

PATENT NO. : 5,033,073

Page 1 of 2

DATED : July 16, 1991

INVENTOR(S) : KENNETH D. FRIDDELL

It is certified that error appears in the above-identified patent and that said Letters Patent is hereby corrected as shown below:

Claim 1, column 11, line 11, after "of" insert --a--;

line 38, change "beat" to --beam--.

Claim 6, column 12, line 24, change "defection" to --detection--.

Claim 12, column 13, line 24, change "disk" to --disks--.

Claim 17, column 14, line 14, after "of" insert --a--;

line 35, after "portions" insert a comma (--,--);

lines 36-37, change "dimensions" to --dimension--.

Claim 27, column 17, line 2, change "disk" to --disks--;

UNITED STATES PATENT AND TRADEMARK OFFICE
CERTIFICATE OF CORRECTION

PATENT NO. : 5,033,073

DATED : July 16, 1991

INVENTOR(S) : KENNETH D. FRIDDELL

It is certified that error appears in the above-identified patent and that said Letters Patent is hereby corrected as shown below:

Claim 27, col. 17, line 3, change "aperture" to --apertures--.

Signed and Sealed this

Fifth Day of January, 1993

Attest:

DOUGLAS B. COMER

*Attesting Officer*    Acting Commissioner of Patents and Trademarks